United States Patent [19]

Schwartz

[11] Patent Number: 4,910,202

[45] Date of Patent: Mar. 20, 1990

[54] AMINOMETHYLPHENOLIC PYRAZINES

[75] Inventor: John A. Schwartz, Wilmington, Del.

[73] Assignee: ICI Americas Inc., Wilmington, Del.

[21] Appl. No.: 198,946

[22] Filed: May 26, 1988

[30] Foreign Application Priority Data

May 26, 1987 [GB] United Kingdom ............... 8712365
Mar. 2, 1988 [GB] United Kingdom ............... 8804983

[51] Int. Cl.$^4$ ................. A61K 31/495; C07D 241/20
[52] U.S. Cl. ........................................ 514/255; 544/407
[58] Field of Search ..................... 544/407; 514/255

[56] References Cited

U.S. PATENT DOCUMENTS

| | | | |
|---|---|---|---|
| 3,305,552 | 2/1967 | Cragoe et al. | 260/250 |
| 3,544,568 | 12/1970 | Cragoe, Jr. et al. | 260/247.2 |
| 3,555,024 | 1/1971 | Cragoe, Jr. et al. | 544/407 |
| 3,567,725 | 3/1971 | Grabowski et al. | 544/407 |
| 3,577,418 | 5/1971 | Cragoe, Jr. et al. | 260/250 |
| 3,809,721 | 5/1974 | Schultz et al. | 260/570.9 |
| 3,928,624 | 12/1975 | Cragoe, Jr. et al. | 260/570.9 |
| 4,029,816 | 6/1977 | Cragoe, Jr. et al. | 260/433 |
| 4,041,032 | 8/1977 | Murakami et al. | 544/407 |
| 4,085,211 | 4/1978 | Cragoe, Jr. et al. | 424/250 |
| 4,115,573 | 9/1978 | Crogoe, Jr. et al. | 544/407 |
| 4,272,537 | 6/1981 | Woltersdorf, Jr. et al. | 544/207 |
| 4,399,138 | 8/1983 | Barlow et al. | 544/407 |
| 4,550,111 | 10/1985 | Barlow et al. | 544/407 |

FOREIGN PATENT DOCUMENTS

| | | | |
|---|---|---|---|
| 86564 | 8/1983 | European Pat. Off. | |
| 57572 | 8/1987 | European Pat. Off. | 544/407 |
| 1181288 | 2/1970 | United Kingdom . | |

OTHER PUBLICATIONS

Cragoe, Jr. Diuretics, Chemistry, Pharmacology, and Medicine, pp. 268–362 (1983).

*Primary Examiner*—Mukund J. Shah
*Assistant Examiner*—Cecilia Shen
*Attorney, Agent, or Firm*—Rosemary M. Miano; Thomas E. Jackson; James T. Jones

[57] ABSTRACT

This invention comprises novel pyrazine amides which are useful as eukalemic diuretics.

9 Claims, No Drawings

AMINOMETHYLPHENOLIC PYRAZINES

BACKGROUND OF THE INVENTION

This invention comprises novel aminomethylphenolic pyrazines which are useful as eukalemic diuretics.

A variety of agents are available for use in treating hypertension. One particular class of such agents is diuretics. Diuretics are used for a variety of purposes, for example, reduction of fluid from the body and reduction of soduum levels in the body, for example, in the treatment of hypertension and edema. An example f a diuretic is 2-(aminomethyl)-4-(1,1-dimethylethyl)-6-iodophenol hydrochloride of formula I: (Formula set out on pages following Examples) I discussed in U.S. Pat. No. 4,029,816 to Cragoe et al; and Stokker, G.E., *J. Med. Chem.*, 1980, 23, 1414–1427. Additional diuretics include hydrochlorothiazide and chlorthalidone.

A problem with some diuretics is the reduction of serum potassium levels and complications caused from reductions of potassium beyond levels needed for maintaining hhysiological functions. Thus, some diuretics are used in conjunction with a potassium conserving agent such as 3,5-diamino-N-(aminoiminomethyl)-6-chloropyrazine carboxamide monohydrochloride, dihydrate of formula II: (Formula set out on pages following Examples) II shown in U.S. Pat. No. 3,577,418 to Cragoe et al which is used in conjunction with, for example, thiazide diuretics.

There is thus a need for a single agent which is an effective but potassium-conserving (isokalemic, also called eukalemic) diuretic, such that it obviates the problems associated with hypokalemia (potassium depletion) and hyperkalemia (potassium buildup) without the need for taking multiple therapeutic agents.

A series of pyrazinecarboxamides has been described in U.S. Pat. 4,085,411 as eukalemic agents possessing diuretic and natriuretic properties. We have now discovered (and this is a basis for our invention) that, surprisingly, certain aminomethylphenol containing pyrazine amides of the formula III defined below possess eukalemic diuretic properties and are of value in treating those diseases and conditions in which a eukalemic diuretic effect is required, for example in treating edema, hypertension and/or related conditions.

SUMMARY OF THE INVENTION

The invention comprises compounds of formula III: (Formula set out on pages following Examples) III wherein:

$R^4$ is selected from a group consisting of hydrogen and (1-5C)alkyl;

$R^6$ is selected from a group consisting of bromo, iodo and t-butyl;

$R^7$ is chloro, hydrogen, (1-5C)alkyl or (1-3C)alkyl ether (also known as (1-3C)alkoxy);

$R^8$ is hydrogen, (1-5C)alkyl, or (1-3C)alkyl ether provided that when $R^6$ is bromo or iodo, then one or both of $R^7$ and $R^8$ are (1-3C)alkylether and when $R^7$ is chloro, $R^6$ is t-butyl and $R^8$ is hydrogen;

A is selected from a group consisting of chloro and bromo;

Z is selected from a group consisting of chloro, bromo, iodo, trifluoromethyl, $SO_2CH_3$ and $SO_2NR^{10}R^{11}$ where $R^{10}$ and $R^{11}$ are each independently selected from a group consisting of hydrogen and (1-5C)alkyl; and pharmaceutically acceptable salts thereof.

Particular values for $R^4$ when it is a (1-5C)alkyl group include methyl, ethyl and propyl.

Particular values for $R^7$ when it is a (1-5C)alkyl group and when $R^7$ is a (1-3C)alkylether, particular values include methoxy and ethoxy.

Particular values for $R^8$ when it is a (1-5C)alkyl group include methyl, ethyl and propyl; and when $R^8$ is a (1-3C)alkylether, particular values include methoxy and ethoxy.

Particular values for $R^{10}$ or $R^{11}$, independently, when it is a (1-5C)alkyl group include methyl, ethyl and propyl.

More particular values for the groups described above consist of:

for $R^4$ hydrogen and (1-3C)alkyl;
for $R^6$ bromo and t-butyl;
for $R^7$ and $R^8$ (independently): hydrogen and methoxy;
for A: chloro and bromo;
for Z: bromo and $SO_2CH_3$.

Even more particular values for some of the groups described above consist of:

for $R^4$: hydrogen and methyl;
for $R^6$: t-butyl (preferred);
for A: chloro; and
for Z: bromo;

Preferred compounds are:

(a) 3,5-diamino-N-[2-[[2-[[[3-bromo-5-(1,1-dimethylethyl)-2-hydroxyphenyl]methyl]amino]ethyl]methylamino]ethyl]-6-chloropyrazinecarboxamide; and (b) 3,5-diamino-6-chloro-N-[2-[[2-[[[5-(1,1-dimethylethyl)-2-hydroxy-3-(methylsulfonyl)phenyl]methyl]amino]ethyl]methylamino]ethyl]pyrazinecarboxamide.

It will be appreciated that certain of the compounds of formula III, for example those containing an asymmetrically substituted carbon atom may exist in, and be isolated in, optically-active and racemic forms. Some compounds may exhibit polymorphism. It is to be understood that the present invention encompasses any racemic, optically-active, tautomeric, polymorphic or stereoisomeric form, or mixtures thereof, which form possesses the properties described above, it being well known in the art how to prepare optically-active forms (for example, by resolution of the racemic form or by synthesis from optically-active starting materials).

In this specification $R^4$, $R^7$ et cetera stand for generic radicals and have no other significance. It is to be understood that the generic term "(1-5C)alky" includes both straight and branched chain alkyl radicals but references to individual alkyl radicals such as "propyl" embrace only the straight chain ("normal") radical, branched chain isomers such as "isopropyl" being referred to specifically.

The compounds of formula III of the present invention may be prepared by methods which include those known in the art. For the methods described below "Pyz" has the meaning shown in formula IV:

(Formula set out on pages following Examples) IV
These methods include the following:

(A) Reductively alkylating a particular pyrazinamidoamine of formula VIII:
(Formula set out on pages following Examples) VIII with an appropriate salicylaldehyde of formula XI:

(Formula set out on pages following Examples) XI in a solvent such as ethanol or methanol by in situ formation of an intermediate imine of formula XII:

(Formula set out on pages following Examples) XII (which is formed but not isolated) and reduction with a reducing agent such as sodium borohydride or hydrogen and a catalyst. The desired reaction product is recovered by diluting the reaction mixture with water to precipitate the product, which may be purified by crystallization from an appropriate solvent, such as methanol or ethanol.

(B) Alkylating a pyrazinamidoamine of formula VIII with a benzyl halide of formula XIV:

(Formula set out on pages following Examples) XIV and, preferably, in the presence of a base such as, for example, potassium carbonate or triethylamine, for example, for 1 to 5 days at, for example, room temperature. A solvent such as methanol or dimethylformamide is used. The desired reaction product is isolated by diluting the reaction mixture with water to precipitate the product, which may be purified by crystallization from an appropriate solvent, such as methanol or ethanol.

(C) Reacting a pyrazinamidoamine of formula VIII with a phenol of formula XV:

(Formula set out on pages following Examples) XV and formalin solution and heating at temperatures up to 100° C. for 1 to 5 days. A solvent such as tetrahydrofuran or dioxane is used. The desired reaction product is recovered by evaporation of the solvent and purified by crystallization from an alcohol such as ethanol.

(D) Reacting a benzylic triamine of formula XVI:

(Formula set out on pages following Examples) XVI with a pyrazinoyl imidazole of formula V. The desired reaction product may be recovered by diluting the reaction mixture with water to precipitate the product, which may be purified by crystallization from an appropriate solvent, such as methanol or ethanol.

(E) Halogenating a selected aminomethylphenolic pyrazine (corresponding to a compound of formula III but with Z=hydrgen, prepared by analogy with method (A), (B) or (D) above) with a halogenating agent in a solvent such as acetic acid or methylene chloride. The desired product is recovered by evaporation of the solvent and crystallization from an appropriate solvent such as methanol or ethanol.

(F) Dealkylating a selected O-alkyl aminomethylphenolic pyrazine derivative of formula XVIII:

(Formula set out on pages following Examples) XVIII (where $R^9$ is lower alkyl, for example, methyl) (prepared by an analogous method to one described above in method (A), (B) or (D) for compounds of formula III) with a dealkylating agent such as lithium thioethoxide or boron tribromide in a solvent such as dimethylformamide or methylene chloride respectively. The desired reactio product may be recovered by diluting the reaction mixture with water to precipitate the product, which may be purified by crystallization from an appropriate solvent, such as methanol or ethanol.

The benzylic triamines of formula XVI are prepared by mixing the particular aliphatic triamine of formula XIII (see U.S. Pat. No. 3,201,472 as an example of how to make selected aliphatic triamines) with an appropriate salicylaldehyde of formula XI in a solvent such as ethanol or methanol. The intermediate imines of formula XVII which are formed are not isolated but stirred with a reducing agent such as sodium borohydride or hydrogen and a catalyst. The desired reaction product is recovered by diluting the reaction mixture with water to precipitate the product, which may be purified by crystallization from a hydrocarbon solvent.

Pyrazinoid acids of formula $PyzCO_2H$ are prepared by the hydrolysis of the corresponding methyl esters of formula $PyzCO_2CH_3$. The hydrolysis is uusually carried out using a solution of aqueous base such as sodium hydroxide and a solvent such as isopropanol or ethanol and stirring the mixture at room temperature for one to 24 hours. The pyrazinoic acid is then isolated by cooling and acidifying the mixture with an acid such as hydrochloric acid.

The pyrazinoyl imidazoles of formula V:

(Formula set out on pages following Examples) V are prepared by reacting the corresponding acids of formula $PyzCO_2H$ with 1,1-carbonyldiimidazole (slight excess) in a solvent such as dimethylformamide or methanol at room temperature and stirring the mixture for 10 to 24 hours. The pyrazinoyl imidazoles are isolated by dilution with methanol or water.

The pyrazinamides of formula VI:

(Formula set out on pages following Examples) VI are prepared by mixing the particular pyrazinoyl imidazole with an alphatic diamine of formula VII:

(Formula set out on pages following Example) VII and stirring at ambient temperature for 5 to 24 hours. A solvent such as tetrahydrofuran may be added or an excess of the diamine may be used as the solvent. The desired reaction product is recovered by evaporating the solvent to provide the product which can be purified by crystallization from an alcohol such as ethanol.

Alternatively, pyrazinamides of formula VI can be prepared by mixing the particular pyrazinoic acid methyl ester with an excess of the aliphatic diamine of formula VII and heating at temperatures up to 100° C. for 1 to 24 hours. The desired reaction product is recovered by evaporation of the excess diamine.

Pyrazinamidoamines of formula VIII:

(Formula set out on pages following Examples) VIII are prepared by mixing an aliphatic haloamine of formula IX:

(Formula set out on pages following Examples) IX where L is iodo, bromo or chloro and Q is a suitable protecting group, for example, phthalimide or butyloxycarbonyl (BOC) such as in formula IXa:

(Formula set out on pages following Examples) IXa with the particular pyrazinamide of formula VI and a base such as potassium carbonate or triethylamine for 1 to 5 days at room temperature. A solvent such as methanol or dimethylformamide is used. The protected pyrazinamidoamine of formula X:

(Formula set out on pages following Examples) X is isolated by diluting with water. It can be purified by recrystallization from an appropriate solvent such as ethanol. Removal of the protecting group provides the desired pyrazinamidoamine of formula VIII:

(Formula set out on pages following Examples) VIII Pyrazinamidoamines of formula VIII may also be prepared by mixing the particular pyrazinoyl imidazolide with an excess of an aliphatic triamine of formula XIII:

(Formula set out on pages following Eamples) XIII in a solvent such as tetrahydrofuran. The desired reaction product is recovered by evaporating the solvent to provide the product.

Pharmaceutically acceptable salts may be obtained using standard procedures well known in the art, for example, by reacting a compound of formula III with a suitable acid affording a physiologically acceptable anion, such as, for example, sulfuric acid, hydrochloric acid or citric acid.

As stated previously, the compounds of this invention or a salt thereof may be useful in the treatment of hypertension or edema and particularly as diuretics, especially eukalemic diuretics. The compounds of formula III are of value as pharmacological standards for the development and standardization of new disease models and assays for use in developing new therapeutic agents for treating hypertension.

When used in the treatent of one or more of the above mentioned diseases, accompound of formula III or a salt thereof may generally be administered as an appropriate pharmaceutical composition which comprises a compound of formula III as defined hereinbefore or a salt thereof together with a pharmaceutically acceptable diluent or carrier, the composition being adapted for the particular route of administration chosen. Such compositions are provided as a further feature of the invention. They may be obtained by employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically acceptable inert solid diluents such as lactose.

For oral administration a tablet or capsule containing up to 250 mg (and typically 5 to 100 mg) of a compound of formula III or a salt thereof may conveniently be used. Similarly, for intravenous or intramuscular injection or infusion a sterile solution or suspension containing up to 10% w/w (and typically 0.05 to 5% w/w) of a compound of formula III or a salt thereof may conveniently be used.

The dose of compound of formula III or a salt thereof to be administered will necessarily be varied according to principles well known in the art taking account of the route of administration and the severity of the condition and the size and age of the patient under treatment. However, in general, a compound of formula III or a salt thereof will be administered to a warm-blooded animal (such as man) so that a dose in the range of, for example, 0.05 to 25 mg/kg (and usually 0.5 to 10 mg/kg) is received.

The diuretic and eukalemic properties of a compound of formula III may be demonstrated by using standard tests.

TEST A

Method

Female Beagle dogs are selected from an established breeding colony (weight range 9.0–13.0 kg), placed on a special diet of certified dog food and one can of Prescription Diet P/D Dog Food, and observed for suitability for training. Dogs are selected from this group for training. Over a one to two week period the dogs are allowed to gradually build up tolerance to light restraint, standing, or sitting in a mesh sling support stand. Maximum time in sling is approximately 9 hours. Also, relaxed acceptance of the process of urinary bladder catheterization is accomplished during the training period. Sterile Bardex foley catheters (sizes 8, 10 pediatric) are used. The conscious female Beagle dogs with free access to water are fasted overnight. The dogs are placed in sling support stands (Alice King Chatham) and catheterized. A short equilibration period of about 30 minutes allows time for residual urine to be drained from the bladder. Urine spontaneously voided is collected in 50 ml pre-weighed tubes (Falcon). Two 1-hour control periods are followed by oral dosing with gelatin capsules containing test compounds or standard diuretics. Alternatively, some compounds are administered via oral gavage tubes in 10 ml quantities. No water loading is done. Spontaneously voided urine is collected for an additional six hours for a total collection period of eight hours. Afterward, dogs are returned to cages and fed and watered. Experiments are conducted once every two weeks on each dog, thus assuring adequate recovery between tests. Urine sample are weighed and measured for volume. Analysis of urinary electrolytes (sodium, potassium chloride) is done on the following day. The analysis of urinary electrolytes showed results similar to other diuretics except that there was no excessive potassium loss.

TEST B

Method

Beagle dogs obtained from the established breeding colony of Marshall Animal Facility or White Eagle Laboratries are utilized. Healthy male and/or female Beagles 9–13 kg in body weight are housed according to standard operating procedure (SOP) for Veterinary Services and are placed on a diet of "certified" dry dog food supplemented with one can of puppy diet P/D Prescription Diet dog food, with free access to water. A two-week minimum period of equilibration on this diet is necessary beore determination of basal level electrolytes is attempted.

Prior to beginning actual drug dosing, six control blood samples are obtained to etablish a range for basal level electrolytes. Control samples are evaluated for consistency in plasma $K^{30}$ levels, and a range of less than 0.25 mEq of $K^+$ is usually desirable. Historically, plasma $K^+$ levels in the range of 4.00–4.30 mEq have been obtained. Any dog not approximating these values is normally dropped from the study.

Sampling Procedure

Plasma samples are obtained by forearm venopuncture via the saphenous vein or the jugular vein. A 5 cc syringe with 20 gauge needle is used to obtain one 5 cc sample. The sample is preserved with 100 $\mu$l of 1000 unit heparin. Samples are centrifuged for ten minutes at 2500 rpm. Plasma is then pipetted into an appropriately labeled tube and all samples are frozen to await electrolytes determination.

Drug Dosing Schedule and Preparation

After control samples are analyzed, the dogs are divided randomly into groups, allowing a minimum of four dogs per drug group. Test compounds are dosed on a mg/kg basis. Gelatin capsules size "2"00 and "3"000 are used. Alternatively, some compounds are administered via oral gavage tubes. Compounds are suspended in 10 ml of saline by sonicating. The weight of the dog is determined by averaging the values over the three days of controls. Time of day for drug dosing is consistent throughout the study. Samples are required on days 4, 7, 11, 14, 21, and 28. Dosing takes place mid-morning (10 a.m. to 11 a.m.), and blood is drawn approximately three hours after dosing (1 p.m. to 2 p.m.). (Drug capsules are dosed orally followed by 5–10 cc of water from a syringe with oral dosing needle attached.) Hematocrits are taken with Microhematocrit capillary tubes and read immediately following collection of plasma samples.

Data Evaluation

Plasma samples are analyzed for potassium as described above and showed no substantial change in serum potassium.

In general, the compounds of this invention which were tested showed a profile as a eukalemic diuretic. Compounds of this invention which were tested have not shown any signs of overt toxicity following oral administration at a dose several multiples of the recommended therapeutic dose.

The invention will now be illustrated by the following non-limiting examples in which, unless stated otherwise:

(i) temperatures are given in degrees Celsius (C); operations were carried out at room or ambient temperature, that is, at a temperature in the range of 18°–25°;

(ii) evaporation of solvent was carried out using a rotary evaporator under reduced pressure (600–4000 pascals; 4.5–30 mm Hg) with a bath temperature of up to 60°;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, DE USA;

(iv) in general, the course of reactions was followed by TLC and reaction times are given for illustration only;

(v) melting points are uncorrected and (d) indicated decomposition; the melting points given are those obtained for the materials prepared as described; polymorphism may result in isolation of materials with diferent melting points in some preparations;

(vi) all final products were essentially pure by TLC and microanalytical data;

(vii) yields are given for illustration only;

(viii) reduced pressures are given as absolute pressures in pascals (Pa.); other pressures are given as gauge pressuresin bars;

(ix) chemical symbols have their usual meanings; the following abbreviations have also been used: v (volume), w (weight), mp (melting point), l [liter(s)], ml (milliliters), g [gram(s)], mg [milligram(s)];

(x) solvent ratios are given in volume: volume (v/v) terms;

(xi) TLC solvent systems: Solvent System A: 25:5:70 (v/v/v) methanol:triethylamine:methylene chloride;

(xii) some compounds are denoted by letters for Example (A), for later reference in the Examples; and (xiii) drying the organic phase was accomplished by swirling with sodium sulfate.

EXAMPLE 1

3,5-Diamno-N-[2-[[2-[[[3-bromo-5-(1,1-dimethylethyl)-2hydroxyphenyl]methyl]amino]ethyl]methylamino]ethyl]-6-chloropyrazinecarboxamide (Formula III, A=Cl, $R^7=R^8=H$, $R^4=CH_3$, Z=Br, $R^6=C(CH_3)_3$).

(a) A solution of 1.52 g (3.74 mmol) of 3,5-diamino-N-[2-[(2-aminoethyl)methylamino]ethyl]-6-chloropyrazinecarboxamide trihydrochloride (A) in 100 ml of 95% aqueous ethanol was neutralized with 1.7 g (20.0 mmol) of sodium bicarbonate. To this slurry was added 1.15 g (4.5 mmol) of 2-hydroxy-3-bromo-5-(1,1-dimethylethyl)benzaldehyde (see L. C. Felton and J. H. Brewer, *Science*, 105:409 (1947) as an example of how to obtain this material). After stirring for 18 hours at ambient temperature, 0.23 g (5.0 mmol) of sodium borohydride was added. After 2 hours, the solvent was evaporated. The residue was partitioned between water and methylene chloride. The organic phase was dried and evaporated. The residue was chromatograped on silica gel (50 g) using 4:96 (v/v) methanol:methylene chloride as eluent. There was obtained 1.18 g (2.23 mmol, 59%) of the title compound as a light yellow solid; mp 131.5°–132° C.

Analysis calculated for; $C_{21}H_{31}BrClN_7O_2$: C, 47.69; H, 5.91; N, 18.54; Found: C, 47.72; H, 6.03; N, 18.52.

(b) The starting material (A) was obtained as follows:

(1) A mixture of 20 g (99.0 mmol) of methyl 3,5-diamino-6-chloropyrazine-2-carboxylate (see U.S. Pat. No. 4,029,816 for an example of how to obtain this material) and 17 g (230.0 mmol) of N-methylethylenediamine was heated at reflux under an inert atmosphere for 30 hours. The rection mixture was cooled to ambient temperature and the solid was dissolved in 100 ml of tetrahydrofuran. The solution was filtered and evaporated. The residue was crystallized from 2-propanol. There was obtained 15.0 g (61.2 mmol, 61%) of 3,5-diamino-6-chloro-N-(2-methylaminoethyl)pyrazine-2-carboxamide; mp 142.5°–143° C.

Analysis calculated for; $C_8H_{13}ClN_6O$: C, 39.27; H, 5.35; N, 34.35; Found: C, 39.28; H, 5.26; N, 34.55.

(2) A mixture of 3.6 g (14.7 mmol) of 3,5-diamino-6-chloro-N-(2-methylaminoethyl) pyrazine-2-carboxamide, 3.3 g (14.7 mmol) of 2-[(tert-butoxycarbonyl)amino]ethyl bromide (see V. G. Beylin and O. P. Goel, Organic Preparations and Procedures International, 19:78 (1978) as an example of how to obtain this material) and 2.1 g (14.8 mmol of potassium carbonate in 25 ml of dimethylformamide was stirred for 18 hours at ambient temperature. The reaction mixture was diluted with 300 ml of water and the solids were filtered and air dried. The solid was chromatographed on 50 g of silica gel eluted with 3:97 (v/v) methanol: methylene chloride. There was obtained 3.3 g (8.5 mmol, 58%) of 2-[[(3,5-diamino-6-chloropyrazinyl)carbonyl]amino]ethyl]methylamino]-ethyl]carbamic acid 1,1-dimethylethyl ester as a white solid after recrystallization from 2-propanol; mp 160°–160.5° C.

Analysis calculated for; $C_{15}H_{26}ClN_7O_3$: C, 46.45; H, 6.76; N, 25.28; Found: C, 46.36; H, 6.76; N, 25.28.

(3) A solution of 2.0 g (5.15 mmol) of [2-[[(3,5-diamino-6-chloropyrazinyl)carbonyl]amino]-ethyl]methylamino]ethyl]carbamic acid 1,1-dimethylethyl ester in 50 ml of ethanol was saturated with hydrogen chloride for 10 minutes. The solvent was evaporated and the residue triturated with ether. There was obtained 1.52 g (4.21 mmol, 73%) of 3,5-diamino-N-[2-[2-aminoethyl)- methylamino]ethyl-6-chloropyrazinecarboxamide trihydrochloride as a light yellow solid. $R_f$=0.45, Solvent Sysem A.

Analysis calculated for; $C_{10}H_{18}ClN_7O.3HCl.3-H_2O.C_2H_5OH$: C, 30.09; H, 5.49; N, 24.08; Found: C, 30.07; H, 5.36; N, 23.91.

(c) To 17.0 g (32.14 mmol) of 3,5-diamino-N-[2-[[2-[[[3-bromo-5-(1,1-dimethylethyl)-2-hydroxyphenyl]methyl]amino]ethyl]methylamino]ethyl]-6-chloropyrazinecarboxamide made by the method of Example 1(a) in 50 ml of ethanol was added 32.14 ml (64.28 mmol) of 2N hydrochloric acid. The solution was evaporated and the residue crystallized from ethanol providing 16.7 g (27.31 mmol, 85%) of a dihydrochloride salt; mp 167°–168° C.

Analysis calculated for; $C_{21}H_{31}BrClN_7O_2.2HCl.\frac{1}{2}H_2O$: C, 41.29; H, 5.60, N, 16.05; Found: C, 41.44; H, 5.40; N, 16.14.

(d) To 10.0 g (18.9 mmol) of 3,5-diamino-N-[2-[[2-[[[3-bromo-5-(1,1-dimethylethyl)-2-hydroxyphenyl]methyl]amino]ethyl]methylamino]ethyl]-6-chloropyrazinecarboxamide made by the method of Example 1(a) dissolved in 200 ml of boiling ethanol was added 3.65 g (19.0 mmol) of citric acid. The volume was concentrated to 150 ml and the solution was cooled. There was obtained 12.1 g (16.6 mmol, 88%) of the citrate salt; mp 172°–173° C. Analysis calculated for; $C_{21}H_{31}BrClN_7O_2.C_6H_8O_7$: C, 44.98; H, 5.45; N, 13.60; Found: C, 44.65; H, 5.41; N, 13.51.

(e) To 9.62 g (18.18 mmol) of 3,5-diamino-N-[2-[[2-[[[3-bromo-5-(1,1-dimethylethyl)-2-hydroxyphenyl]methyl]amino]ethyl]methylamino]ethyl]-6-chloropyrazinecarboxamide made by the method of Example 1(a) dissolved in 225 ml of boiling ethanol was added 3.60 g (40.0 mmol) of oxalic acid. The solution was cooled and there was obtained 10.53 g (14.85 mmol, 82%) of the oxalate salt; mp 192°–194° C.

Analysis for; $C_{21}H_{31}BrClN_7O_2.2C_2H_2O_4$ Calculated: C, 42.35; H, 4.98; N, 13.83; Found: C, 42.44; H, 4.95; N, 14.08.

(f) A mixture of .53 g (1.0 mmol) of 3,5-diamino-N-[2-[[2-[[[3-bromo-5-(1,1-dimethylethyl)-2hydroxyphenyl]methyl]amino]ethyl]methylamino]ethyl]-6-chloropyrazinecarboxamide made by the method of Example 1(a) and 2 ml of 1N sulfuric acid in 30 ml of ethanol was brought to reflux and then cooled to ambient temperature. The solid was filtered and dried. There was obtained 0.605 g (0.95 mmol, 95%) of the sulfate salt; mp 210°–212° C. Analysis for; $C_{21}H_{31}BrClN_7O_2.H_2SO_4.\frac{1}{2}H_2O$ Calculated: C, 39.66; H, 5.38; N, 15.42; Found: C, 39.53; H, 5.18; N, 15.04.

EXAMPLE 2

3,5-Diamino-N-[2-[[2-[[[3,5-dibromo-4,6-dimethoxy-2-hydroxphenyl]methyl]amino]ethyl]methylamino]ethyl]-6-chloropyrazinecarboxamide (Formula III, A=Cl, $R^4$=CH$_3$, Z=Br, $R^8$=OCH$_3$, $R^7$=OCH$_3$, $R^6$=Br).

(a) A solution of 1.74 g (6.00 mmol) of 3,5-diamino-N-[2-[(2-aminoethyl)methylamino]ethyl]-6-chloropyrazinecarboxamide (B) and 2.05 g (6.02 mmol) of 2-hydroxy-3,5-dibromo-4,6-dimethoxybenzaldehyde (C) in 50 ml of methanol was stirred at ambient temperature for 1 hour. Sodium borohydride (0.38 g, 10.0 mmol) was added and the reaction mixture stirred for 1 hour. The solution was evaporated and the residue was partitioned between water and methylene chloride. The organic phase was dried and evaporated. The residue was chromatographed on 150 g of silica gel eluted with 2:98 (v/v) methanol:methylene chloride. There was obtained 2.25 g (3.68 mmol, 61%) of the title compound as a white solid after trituration with ether-hexane; mp 113°–114° C. This compound was converted into an oxalate salt with oxalic acid in methanol; mp 180°–181° C.

Analysis calculated for; $C_{19}H_{26}Br_2ClN_7O_4.2C_2H_2O_4$: C, 34.89; H, 3.82; N, 12.38; Found: C, 34.83; H, 3.85; N, 12.59.

(b) The starting material (B) was obtained as follows:

To a stirred solution of 84.0 g (0.744 mol) of N-(2-aminoethyl)-N-methyl-1,2-ethanediamine (see U.S. Pat. No. 3,201,472 for an example of how to obtain this material) in 700 ml of tetrahydrofuran was added 88.6 g (0.372 mol) of 1-(3,5-diamino-6-chloropyrazinoyl)imidazole in 10 portions over 1.5 hours. After 1 hour at ambient temperature the reaction mixture was filtered and concentrated to 300 ml. The solution was added dropwise to 1.4 liters of ether with vigorous stirring. The solid was filtered, washed with ether and dried. There was obtained 74.3 g (0.258 mol, 70%) of 3,5-diamino-N-2-[(2-aminoethyl)methylamino]ethyl]-6-chloropyrazinecarboxamide. A sample was filtered through a pad of silica gel and eluted with 5:95 (v/v) methanol:methylene chloride saturated wth ammonia gas; mp 138°–139.5° C.

Analysis calculated for; $C_{10}H_{18}ClN_7O$: C, 41.74; H, 6.31; N, 34.07; Found: C, 41.53; H, 6.15; N, 33.72.

(c) The starting material (C) was obtained as follows:

A solution of 1.0 g (3.83 mmol) of 2-hydroxy-3-bromo-4,6-dimethoxybenzaldehyde (see R. Royer, et al, *Eur. J. Med. Chem.*, 12:455 (1977) as an example of how to obtain this material) in 50 ml of glacial acetic acid was warmed to 60° C. N-Bromosuccinimide (0.68 g, 3.83 mmol) was added in one portion and the solution was cooled to ambient temperature. The reaction mixture was diluted with 200 ml of water and the solids were filtered and air dried. The solid was crystallized from ethanol. There was obtained 1.1 g (3.24 mmol, 84%) of 2-hydroxy-3,5-dibromo-4,6-dimethoxybenzaldehyde as a white solid; mp 103°–104° C.

Analysis calculated for; $C_9H_8Br_2O_4$: C, 31.80; H, 2.37; Found: C, 31.87; H, 2.42.

EXAMPLE 3–8

(a) The procedure described in Example 2 was repeated using benzaldehydes of the formula XI to give products of the formula III, where A =Cl, $R^4$=CH$_3$, and $R^6$, $R^7$, $R^8$ and Z have the values shown in Table I.

TABLE I

| Example | $R^7$ | $R^6$ | $R^8$ | Z | mp °C. Free Base | % Yield | Salt | mp °C. Salt |
|---|---|---|---|---|---|---|---|---|
| 3 | H | —C(CH$_3$)$_3$ | H | CF$_3$ | 156.5–157 | 69 | di-HCl | 212–214 |
| 4 | H | —C(CH$_3$)$_3$ | H | SO$_2$CH$_3$ | 174–174.5 | 67 | di-HCl | 180–181 |
| 5 | Cl | —C(CH$_3$)$_3$ | H | Br | 123–125 | 48 | di-HCl | 168–170 |

TABLE I-continued

| Example | R⁷ | R⁶ | R⁸ | Z | mp °C. Free Base | % Yield | Salt | mp °C. Salt |
|---------|----|----|----|----|-----------------|---------|------|-------------|
| 6 | H | —C(CH$_3$)$_3$ | OCH$_3$ | Br | 130-132 | 97 | di-HCl | 158-160 |

(b) the benzaldehyde used in Example 3 was prepared as follows:

A mixture of 3.41 g (15.5 mmol) of 2-trifluoromethyl-4-(1,1-dimethylethyl)phenol (see E. Stokker, et al, *J. Med. Chem.*, 23:1414 (1980) as an example of how to obtain this material) and 2.24 g (16.0 mmol) of hexamethylenetetramine was refluxed in 30 ml of trifluroacetic acid for 5 hours. The solution was cooled to ambient temperature and diluted with 200 ml of water. The aqueous residue was extracted with hexane. The organic phase was washed with saturated sodium bicarbonate solution, dried and evaporated. The residue was chromatographed on 100 g of silica gel using hexane as eluent. There was obtained 1.54 g (6.25 mmol, 40%) of 2-hydroxy-3-trifluromethyl-5-(1,1-dimethylethyl)benzaldehyde as a white solid; mp 56°-57.5° C.

Analysis calculated for; $C_{12}H_{13}F_3O_2$: C, 58.54; H, 5.32; Found: C, 58.80; H, 5.47.

(c) The benzaldehyde used in Example 4 was prepared in a similar manner to that described for Example 3. From 7.40 g (32.4 mmol) of 2-methylsulfonyl-4-(1,1-dimethylethyl)phenol (see German Offenlegungsschrift DE 32 08 190 A1 to Englert et al, assigned to Hoechst AG as an example of how to obtain this material) there was obtained 4.41 g (17.2 mmol, 53%) of 2-hydroxy-3-methylsulfonyl-5-(1,1-dimethylethyl)benzaldehyde; mp 133°-135° C.

Analysis calculated for; $C_{12}H_{16}O_4S$: C, 56.23; H, 6.29; Found: C, 56.11; H, 6.17.

(d) The benzaldehyde used in Example 5 was prepared in a manner similar to that described for

EXAMPLE 3

(1) A mixture of 50 g (0.39 mol) of 3-chlorophenol in 250 ml of hexane and 125 ml of 85% phosphoric acid was heated to reflux. A solution of 43.2 g (0.584 mol) of 2-methyl-2-propanol in 25 ml of hexane was added over 1.5 hours. After addition, the reaction mixture was refluxed for 4 hours. The organic phase was separated and extracted four times with 30 ml of 1N sodium hydroxide solution. The combined aqueous fractions were made acidic and extracted with methylene chloride. The organic phase was dried and evaporated at 90° C. (25 mm). The residue was crystallized from hexane. There was obtained 0.46 g (2.49 mmol, 0.6%) of 3-chloro-4-(1,1-dimethylethyl)phenol as a white solid after crystallization from hexane; mp 65°-67° C.

Analysis calculated for; $C_{10}H_{13}ClO$: C, 65.04; H, 7.10; Found: C, 64.90; H, 6.89.

(2) From 14.2 g (76.9 mmol) of 3-chloro-4-(1,1-dimethylethyl)phenol there was obtained 1.90 g (8.9 mmol, 12%) of 2-hydroxy-5-(1,1-dimethylethyl)-6-chlorobenzaldehyde; mp 69°-71° C.

Analysis calculated; for $C_{11}H_{13}ClO_2$: C, 62.12; H, 6.16; Found: C, 62.13; H, 6.16.

(3) A solution of 1.97 g (9.26 mmol) of 2-hydroxy-5-(1,1-dimethylethyl)-6-chlorobenzaldehyde and 1.98 g (11.1 mmol) of N-bromosuccinimide in 30 ml of methylene chloride was stirred for 2 hours. Water (50 ml) was added. The organic phase was dried and evaporated. The residue was chromatographed on 150 g of silica gel eluted with 1:99 (v/v) ether:hexane. There was obtained 2.69 g (9.22 mmol, 99%) of 2-hydroxy-3-bromo-5-(1,1-dimethylethyl)-6-chlorobenzaldehyde as a white solid after recrystallization from hexane; mp 103°-105° C.

Analysis calculated for; $C_{11}H_{12}BrClO_2$: C, 45.31; H, 4.15; Found: C, 45.06; H, 4.15.

(e) The benzaldehyde used in Example 6 was prepared as follows: (1) To a stirred solution of 2.91 g (16.14 mmol) of 3-methoxy-4-(1,1-dimethylethyl)phenol (see C. J. R. Adderley and F. R. Hewgill, *J. Chem. Soc.,* (C), 1438, (1968) as an example of how to obtain this material) in 65 ml of methylene chloride and cooled in an ice-water bath was added 6.12 g (3.54 ml, 32.30 mmol) of titanium (IV) chloride followed by 3.06 g (2.41 ml, 26.64 mmol) of 1,1-dichlorodimethyl ether. The reaction mixture was stirred for 10 minutes and then poured into 16 ml of 1N hydrochloric acid. The organic phase was separated, dried and evaporated. The residue was chromatographed on silica gel (146 g) using 1.5:98.5 (v/v) ether,hexane as eluent. There was obtained 2.92 g (14.01 mmol, 87%) of 2-hydroxy-4-methoxy-5-(1,1-dimethylethyl)benzaldehyde as a white solid after crystallization from pentane; mp 75°-78° C.

Analysis calculated for; $C_{12}H_{16}O_3$: C, 69.21; H, 7.74; Found: C, 69.22; H, 7.56.

(2) A solution of 2.56 g (12.3 mmol) of 2-hydroxy 4-methoxy-5-(1,1-dimethylethyl)benzaldehyde and 2.19 g (12.3 mmol) of N-bromosuccinimide in 20 ml of methylene chloride was stirred for 6 hours. Water (50 ml) was added. The organic phase was dried and evaporated. The residue was chromatographed on silica gel (36 g) using 2:98 (v/v) ether/hexane as eluent. There was obtained 2.45 g (8.53 mmol, 69%) of 2-hydroxy-3-bromo-4-methoxy-(1,1-dimethylethyl)benzaldehyde as white crystals after crystallization from cyclohexane; mp 123°-124° C.

Analysis alculated for; $C_{12}H_{15}BrO_3$: C, 50.19; H, 5.27; Found: C, 50.10; H, 5.23.

EXAMPLE 7

3,5-Diamino-N-[2-[[2-[[[3-bromo-5-(1,1-dimethylethyl)-2-hydroxyphenyl]methyl]amino]ethyl]propylamino]ethyl]-6-chloropyrazinecarboxamide (Formula III, A=Cl, R⁷=R⁸=H, R⁴=CH$_2$CH$_2$CH$_3$, Z=Br, R⁶=C(CH$_3$)$_3$).

(a) A solution of 47.31 g (149.8 mmol) of 3,5-diamino-N-[2-[(2-aminoethyl)propylamino]ethyl]-6chloropyrazinecarboxamide (D) and 38.52 g (149.8 mmol) of 2-hydroxy-3-bromo-5-(1,1-dimethylethyl)benzaldehyde in 400 ml of methanol was stirred overnight at ambient temperature. Sodium borohydride (2.84 g, 76.1 mmol) was added. After 1 hour the solvent was evaporated. The residue was partitioned between water and methylene chloride. The organic phase was dried and evaporated. The residue was chromatographed on silica gel (470 g) using a gradient from 1:99 to 5:95 (v/v) of methanol:methylene chloride as eluent. There was obtained 51.36 g (92.2 mmol, 62%) of the title compound as a white solid after crystallization from 2-propanol; mp 148°-149° C.

Analysis calculated for; $C_{23}H_{35}BrClN_7O_2$: C, 49.60; H, 6.33; N, 17.60; Found: C, 49.73; H, 6.25; N, 17.58.

(b) The material from Example 7(a) was converted into a hydrochloride salt and crystallized from 2-propanol; mp 183°–185° C.

Analysis calculated for; $C_{23}H_{35}BrClN_7O_2.2HCl.\frac{1}{2}H_2O$: C, 43.24; H, 5.99; N, 15.35; Found: C, 43.31; H, 5.75; N, 15.30.

(c) The starting material (D) was obtained as follows:

(1) A mixture of 118.6 g (1.67 mol) of acrylamide and 49.3 g (0.83 mmol) of 1-aminopropane in 250 ml of methanol was heated at 80° C. for 1 hour. The solvent was evaporated and the solid crystallized from ethanol. There was obtained 162.3 g (0.81 mol, 97%) of 3,3'-(propylimino)bispropanamide as a white solid; mp 101°–101.5° C.

Analysis calculated for; $C_9H_{19}N_3O_2$: C, 53.71; H, 9.51; N, 20.88; Found: C, 53.94; H, 9.18; N, 20.77.

(2) To a solution of 2.3 liters of 5.25% sodium hypochlorite solution and 580 ml of 10N sodium hydroxide cooled in an ice water bath was added 162.3 g (0.81 mol) of 3,3'-(propylimino)bispropanamide dissolved in 75 ml of water. During the addition internal temperature was maintained at 5° C. The reaction mixture was then heated to 60° C. for 3 hours. The solution was cooled to ambient temperature and 1.084 Kg of sodium hydroxide was added. The aqueous solution was extracted with 2-propanol. The organic phase was dried and evaporated. The residue was fractionally distilled under high vacuum. There was obtained 72.5 g (0.49 mol, 60%) of N-(2-aminoethyl)-N-propyl-1,2-ethanediamine as a colorless liquid; bp 53°–73° C. at 266 Pascals. A sample was converted into an oxalate salt in methanol; mp 171°–172° C.

Analysis caculated for; $C_7H_{19}N_3.3C_2H_2O_4$: C,37.59; H, 6.07;N, 10.12; Found: C, 37.44; H, 6.11; N, 10.28.

(3) A mixture of 23.87 g (100.0 mmol) of 1-(3,5-diamino-6-chloropyrazinoyl)imidazole and 58.51 g (300.0 mmol) of N-(2-aminoethyl)-N-propyl-1,2-ethanediamine in 250 ml of tetrahydrofuran was stirred at ambient temperature overnight. The solvent and excess triamine were evaporated and the residue chromatogaphed on silica gel (150 g) using 1.5:98.5 (v/v) methanol: tetrahydrofuran saturated with ammonia gas as eluent. There was obtained 24.64 g (78.0 mmol, 78%) of 3,5-diamino-N-[2-[(2-aminoethyl)-propylamino]ethyl]-6-chloropyrazinecarboxamide as a yellow solid; mp 91°–94° C.

Analysis calculated for; $C_{12}H_{22}ClN_7O.\frac{1}{4}CH_3OH$: C, 45.44; H, 7.16; N, 30.29; Found: C, 45.77; H, 6.91; N, 30.33.

EXAMPLE 8

3,5-Diamino-N-[2-[[2-[[[3-bromo-5-(1,1-dimethylethyl)-2-hydroxyphenyl]methyl]amino]ethyl]methylamino]ethyl]-6-bromopyrazinecarboxamide (Formula III, A=Br, $R^7=R^8$=H, $R^4$=CH$_3$, Z=Br, $R^6$=C(CH$_3$)$_3$).

(a) A solution of 2.00 g (6.02 mmol) of 3,5-diamino-N-[2-[(2-aminoethyl)methylamino]ethyl]-6-bromopyrazinecarboxamide (N) and 1.86 g (7.23 mmol) of 2-hydroxy-3-bromo-5-(1,1-dimethylethyl)benzaldehyde in 100 ml of ethanol was stirred at ambient temperature for 1 hour. Sodium borohydride (0.28 g, 7.27 mmol) was added and the reaction mixture stirred for 1 hour. The solvent was evaporated and the residue was partitioned between water and methylene chloride. The organic phase was dried and evaporated. The residue was chromatographed on silica gel (150 g) using a gradient from 0.2:3:96.8 to 0.3:5:94.7 (v/v/v) of ammonium hydroxide:methanol:methylene chloride as eluent. There was obtained 1.98 g (3.45 mmol, 57%) of the title compound as a white solid after trituration with ether; mp 136°–137° C.

Analyss calculated for; $C_{21}H_{31}Br_2N_7O_2$: C, 43.99; H, 5.45; N, 17.10; Found: C, 43.97; H, 5.14; N, 17.02.

(b) The starting material (N) was otained as follows:

A mixture of 8.20 g (72.0 mmol) of N-(2-aminoethyl)-N-methyl-1,2-ethanediamine and 6.80 g (24.0 mmol) of 1-(3,5-diamino-6-bromopyrazinoyl)imidazole in 48 ml of tetrahydrofuran was stirred at ambient temperature for 30 minutes. The solution was evaporated and the residue triturated with ether. There was obtained 5.85 g (17.6 mmol, 73%) of 3,5-diamino-N-[2-[(2-aminoethyl)-methylamino]ethyl]-6-bromopyrazinecarboxamide; mp 148°–150° C.

Analysis calculated for; $C_{10}H_{18}BrN_7O.\frac{1}{4}H_2O$: C, 35.67; H, 5.54; N, 29.12; Found: C, 35.78; H, 5.36; N, 28.80.

EXAMPLES 9 and 10

(a) The procedure described in Example 2 was repeated using benzaldehydes of the formula XI to give products of the formula III where A=Cl, $R^4$=CH$_3$, $R^7$ and $R^8$ are each hydrogen, $R^6$ is t-butyl and Z has the values shown in Table II.

TABLE II

| Example | Z | % Yield | salt | mp(°C.)salt |
|---|---|---|---|---|
| 9 | Cl | 25 | di-HCl | 160–162° |
| 10 | I | 28 | di-HCl | 164–166° |

EXAMPLE 11

3,5-Diamino-N-[2-[[2-[[[3-bromo-5-(1,1-dimethylethyl)-2-hydroxyphenyl]methyl]amino]ethyl]methylamino]ethyl]6-chloropyrazinecarboxamide (Formula III, A=Cl, $R^7=R^8$=H, $R^4$=CH$_3$, Z=Br, $R^6$=C(CH$_3$)$_3$).

(a) A mixture of 0.24g (1.01 mmol) of 1-(3,5-diamino-6-chloropyrazinoyl)imidazole and 0.36 g (1.00 mmol) of 2-[[[2-[(2-aminoethyl)methylamino]ethyl]amino]methyl]-6-bromo-4-(1,1-dimethylethyl)phenol in 2 ml of tetrahydrofuran was stirred overnight at ambient temperature. The solution was filtered and evaporated. The residue was partitioned between water and methylene chloride. The organic phase was dried and evaporated. The residue was chromatographed on silica gel (11 g) using 3:97 (v/v) methanol:methylene chloride as eluent. There was obtained 0.46 g (0.87 mmol, 87%) of the title compound which was identical to the material prepared in Example 1.

(b) The starting material 2-[[[2-[(2-aminoethyl)methylamino]ethyl]amino]methyl]-6-bromo-4(1,1-dimethylethyl)phenol was obtained as follows:

(1) A solution of 13.67 g (116.6 mmol) of N-(2-aminoethyl)-N-methyl-1,2-ethanediamine and 10.0 g (38.9 mmol) of 2-hydroxy-3-bromo-5-(1,1-dimethylethyl) benzaldehyde was stirred in 100 ml of ethanol overnight. Sodium borohydride (1.03 g 26.5 mmol) was added and the reaction mixture stirred for 1 hour. The solution was evaporated and the residue was partitioned between water and methylene chloride. The organic phase was dried and evaporated. The residue was crystallized from hexane affording 8.05 g (22.5 mmol, 58%) of 2-[[[2-[(2-aminoethyl)methylamino]-ethyl]amino]methyl]-6-bromo-4-(1,1-dimethylethyl)-phenol; mp 99°–100.5° C.

Analysis calculated for; $C_{16}H_{28}BrN_3O$: C, 53.65; H, 7.88; N, 11.73; Found: C, 53.60; H, 7.83; N, 11.71.

EXAMPLE 12

Capsule

Each capsule contains:

| Material | Quantity/350 mg Blend |
| --- | --- |
| Compound of Formula III | 120.0 mg. |
| Lactose, National Formulary (NF) Fast Flo | 175.0 mg. |
| Sodium starch glycolate, NF | 18.0 mg. |

-continued

| Material | Quantity/350 mg Blend |
| --- | --- |
| Pregelatinized starch, NF | 35.0 mg. |
| Magnesium stearate, NF | 2.0 mg. |

All of the above-listed materials except the magnesium stearate, are screened through a suitable screen, for example, 20 mesh, and blended in a mixer for about 5 minutes. The magnesium stearate is screened through a suitable screen, for example, 40 mesh, and the screened magnesium stearate is then added to the blended materials and mixed for 2 minutes. The blended powder is placed in a suitable and properly labeled container and encapsulated in two-piece hard gelatin capsule (size #0) as required.

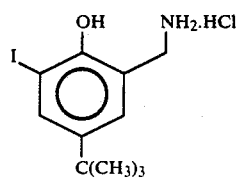  I

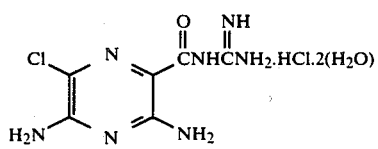  II

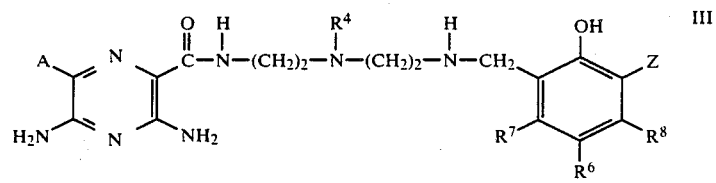  III

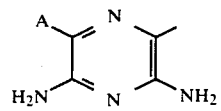  IV

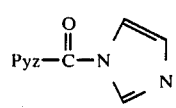  V

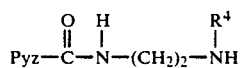  VI

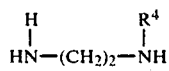  VII

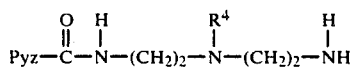  VIII

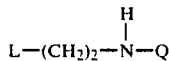  IX

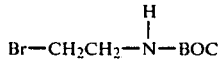  IXa

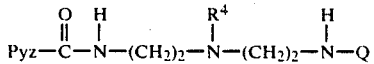  X

-continued
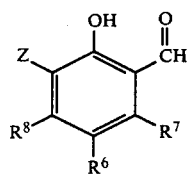
XI
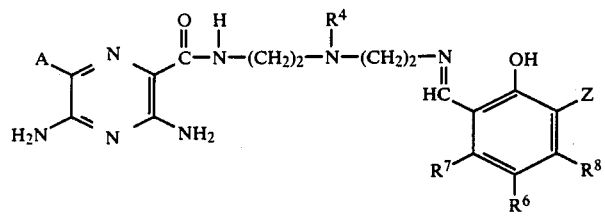
XII
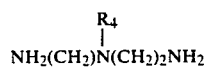
XIII
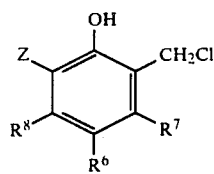
XIV
XV
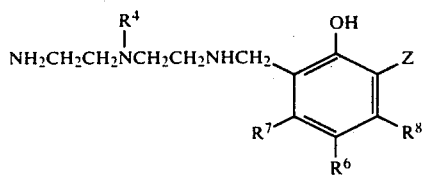
XVI
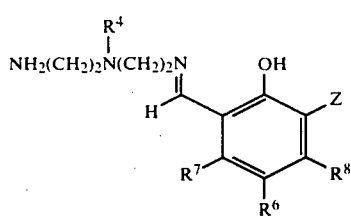
XVII
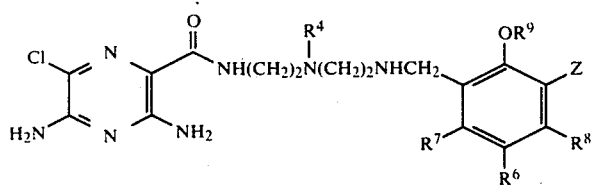
XVIII
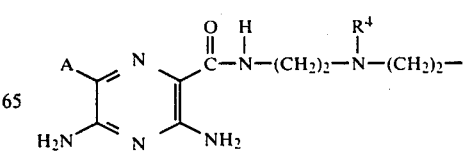
III
What is claimed is:
1. A compound having the formula -continued

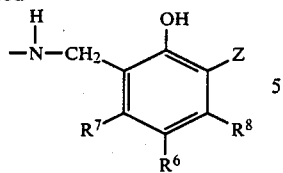

wherein:
$R^4$ is selected from a group consisting of hydrogen and (1-5C)alkyl;
$R^6$ is selected from a group consisting of bromo, iodo and t-butyl;
$R^7$ is chloro, hydrogen, (1-5C)alkyl or (1-3C)alkoxy;
$R^8$ is hydrogen, (1-5C)alkyl, or (1-3C)alkoxy provided that when $R^6$ is bromo or iodo, then one or both $R^7$ and $R^8$ are (1-3C)alkoxy and when $R^7$ is chloro, $R^6$ is t-butyl and $R^8$ is hydrogen;
A is selected from a group consisting of chloro and bromo;
Z is selected from a group consisting of chloro, bromo, iodo, trifluoromethyl, $SO_2CH_3$ and $SO_2NR^{10}R^{11}$ where $R^{10}$ and $R^{11}$ are each independently selected from a group consisting of hydrogen and (1-5C)alkyl; and pharmaceutically acceptable salts thereof.

2. A compound as claimed in claim 1 wherein $R^4$ is hydrogen or (1-3C)alkyl; $R^6$ is bromo or t-butyl; $R^7$ is hydrogen or methoxy; $R^8$ is hydrogen or methoxy; A is chloro or bromo; Z is bromo or $SO_2CH_3$.

3. A compound as claimed in claim 2 wherein $R^4$ is hydrogen or methyl; $R^6$ is t-butyl; A is chloro; and Z is bromo.

4. A compound as claimed in claim 1 selected from:
(a) 3,5-diamino-N-[2-[[2-[[[3-bromo-5-(1,1-dimethylethyl)-2-hydroxyhenyl]methyl]amino]ethyl]methylamino]ethyl-6-chloropyrazinecarboxamide; and
(b) 3,5-diamino-6-chloro-N-[2-[[2-[[[5-(1,1-dimethylethyl)-2-hydroxy-3-(methylsulfonyl)phenyl]methyl]amino]ethyl]methylamino]ethyl]pyrazinecarboxamide, and pharmaceutically acceptable salts thereof.

5. A compound as claimed in claim 2 wherein $R^6$ is t-butyl.

6. A salt as claimed in claim 1 wherein said salt is made with an acid forming a physiologically acceptable anion.

7. A pharmaceutical composition useful as a eukalemic diuretic comprising a eukalemic diuretic amount of a compound of claim 1 or a pharmaceutically acceptable salt thereof an a non-toxic pharmaceutically acceptable diluent or carrier.

8. A method of inducing eukalemic duiresis in a mammal comprising administering to the mammal a pharaceutically effective amount of a compound of claim 1.

9. A method of treating hypertension in a mammal comprising administering a pharmaceutically effective amount of a compound of claim 1 to a mammal in need of such treatment.

* * * * *